United States Patent [19]
Coss et al.

[11] Patent Number: 5,337,638
[45] Date of Patent: Aug. 16, 1994

[54] TORQUE CONTROL RATCHET WRENCH

[75] Inventors: Ronald G. Coss, Newport Beach; Donald J. Hogan, Carlsbad, both of Calif.

[73] Assignee: Micro Motors, Inc., Santa Ana, Calif.

[21] Appl. No.: 16,765

[22] Filed: Feb. 11, 1993

[51] Int. Cl.⁵ .................................... B25B 23/159
[52] U.S. Cl. ................................. 81/483; 173/176; 73/862.21
[58] Field of Search ............... 81/478, 483; 173/176, 173/180, 181; 73/862.21, 862.22, 862.26

[56] References Cited

U.S. PATENT DOCUMENTS

| | | |
|---|---|---|
| 1,033,049 | 7/1912 | Chase et al. . |
| 1,303,595 | 5/1919 | Rifflard . |
| 1,814,544 | 7/1931 | Cairncross et al. . |
| 2,172,561 | 9/1939 | Kruse . |
| 2,704,472 | 3/1955 | Booth . |
| 2,732,747 | 1/1956 | Livermont . |
| 2,743,638 | 5/1956 | Woods . |
| 3,165,014 | 1/1965 | Grabovac . |
| 3,274,827 | 9/1966 | Sturtevant . |
| 3,921,471 | 11/1975 | Smith ................. 87/483 X |

Primary Examiner—James G. Smith
Attorney, Agent, or Firm—Knobe, Martens, Olson & Bear

[57] ABSTRACT

An improved torque wrench for procedures requiring the application of precise small torques. The wrench includes a handle pivotally connected to a cam member rigidly attached to a driving head. The handle breaks out of alignment with the extending cam member upon application of an adjustable torque limit. A spring-biased plunger within the handle normally holds a rigid ball within an elliptical indent in the cam member. Application of the torque limit on the handle forces the ball out of the indent and onto an angled surface before a projecting flange of the handle contacts the cam member and limits the further pivot of the handle. The angled surface provides a reaction force to the ball sufficient to maintain the handle in a pivoted position. The handle pivots a noticeably large angle of 30° before the flange contacts the cam member.

18 Claims, 4 Drawing Sheets

TORQUE CONTROL RATCHET WRENCH

FIELD OF THE INVENTION

The present invention relates to an adjustable torque applying tool, and more particularly to a torque wrench for use in precise torquing operations.

BACKGROUND OF THE INVENTION

Wrenches for limiting an applied torque generally have a head portion with an extending handle. The head portion has a box or other wrench driver and may have a ratchet-like mechanism inside for rapid tightening capability. The handle is used for leverage to turn the head portion and tighten a nut or other fastener until a point at which the nut becomes tight and the handle clicks or slightly slips on application of further torque. An operator, noticing the slippage, then ceases applying further torque. Numerous mechanisms for providing this slip within a torque wrench are known. In particular, U.S. Pat. Nos. 1,814,554, 2,172,561, 2,704,472, 2,732,747, 2,743,368, 3,165,014 and 3,274,827 disclose various torque-limited wrenches.

The most prevalent type of presently available torque-limiting wrenches generally is designed for applications in which accuracy is desired but is not critical. The wrenches operate in such a manner that the user must release pressure on the handle at the exact moment the handle slips, or risk applying an extra increment of torque at the point at which the handle stops slipping. In other words, typical torque wrenches only slip a small distance before the handle again becomes rotationally coupled to the driving head by virtue of a structural handle pivot limit. It is incumbent on the user to swiftly notice the slip and stop the torque on the handle. Wrenches used in torquing car engine bolts or aircraft structural fasteners, for example, must provide a level of accuracy to ensure proper engine performance and stress wear patterns. The torque ranges for such conventional wrenches may be from 5 to 100 foot-pounds though, and accuracy within a foot-pound is considered sufficient. Although an extra amount inadvertently applied by a conventional torque wrench with a large torque capacity is relatively harmless, even a small application of excessive torque assumes a greater importance the lower the torque requirements of a particular fastener becomes.

U.S. Pat. No. 1,303,595 issue to Rifflard discloses a torque wrench having a plunger rod with a fork and a pair of V-shaped nosings shaped to fit within corresponding notches in two star wheels, the wheels being rotationally fixed to a wrench socket wheel. An internally threaded cap regulates the level of compression of a spring acting on the head of the plunger rod. Upon rotation of the handle, and when the reaction torque from a wrench socket reaches a certain point, the nosings cam out of the notches in the star wheels, halting further torquing of the socket. However, to reset the handle once it has been pivoted, the wrench socket wheel must be reoriented with respect to the handle by reducing spring pressure on the plunger rod, in a time-consuming operation.

Thus, despite the existence of prior torque-limiting wrenches, there is a need in certain specialized applications for an improved torque wrench. In dental surgery, for instance, devices for precisely tightening dental prostheses to implants are needed.

In installing a dental prosthesis, a series of drilling steps is necessary to penetrate the jaw bone and prepare the site for the dental implant. Threads are tapped into dense bone and the dental implant (analogous to the root of a tooth) is then either press-fit or screwed into the prepared hole. At this point, a titanium or gold cover screw is inserted into a threaded hole in the implant, and the adjacent tissue sutured over to bury it for three or four months and allow the surrounding bone to set around the implant. Typically, a torque of around 10 Newton-centimeters which is equal to 0.886 inch-pounds, or 0.074 foot-pounds, is used to install the cover screw.

Typically, the dental implant, after subsequent re-exposure, has osseo-integrated into the jaw bone. After removal of the titanium cover screw, an abutment securely attaches to the implant to provide a foundation for the actual dental prosthesis, or tooth. The abutment is either a one-piece screw-in type or is held on the implant with a separate screw, both installed to a particular torque limit. The torque at which the abutment is installed is around 20 Newton-centimeters which is equal to 1.77 inch-pounds, or 0.148 foot-pounds. The dental prosthesis is then usually cemented onto the abutment.

It is extremely important that the abutment be installed to proper torque limits. Clinical experiments have revealed that proper installation torque is important to the quality of the installed dental prosthesis. Too much torque may over stress or strip the bone or dental screw or abutment. Insufficient torque will not ensure a sufficient purchase into the bone possibly causing the screw or abutment to loosen, requiring a follow up re-tightening procedure. In the past, the abutments have been installed by hand with no torque-control hand tools. This process resulted in a widely varying range of torque being applied, feasibly by the same dentist on the same day. Due to the awkward position assumed by the dental surgeon, the extremely low torque limits and the non-stationary and unique work area of a patient's mouth, first estimating, and then repeating a particular application of torque is problematic at best. Typically, the surgeon is reluctant to apply too much torque and the screw or abutment subsequently works itself loose.

The present invention provides an improved torque-limiting tool for highly accurate applications which overcomes the deficiencies of prior art wrenches.

SUMMARY OF THE INVENTION

The present invention provides an improved torque control ratchet wrench for use in precision torque-applying situations, such as in dental surgery. The wrench may be used to install a dental implant into a tapped hole or install one-piece dental abutments into the implant, both procedures having precise limits on the amount of torque which can be applied.

The wrench comprises a head having an internal ratchet drive and a torque-applying handle incorporating a torque-limiting mechanism. The driving head has two possible modes upon handle rotation. Rotation of the torque handle in one direction will be free-spinning and upon rotation of the handle in the opposite direction, the driving head provides a positive driving action.

According to the present invention a torque mechanism includes a stub arm forming a cam member rigidly attached to the head and having a pin axis on which the end of the torque handle assembly nearest the head pivots. The handle and the arm provide a "breakable"

connection between the two. In a preferred form, the hollow torque handle assembly consists of an outer housing, a plunger, a ball, a spring and a set screw. The spring acts against the plunger to bias the ball into a preferably ellipse-shaped indent in the stub arm. The adjustable set screw provides a stop for the spring to modulate the force biasing the plunger toward the elliptical indent.

When the torque handle is rotated in the drive mode, a pre-set calibrated torque is reached and the ball slips out of the stub arm indent. The torque handle includes a relief structure on its radially inner end to allow the handle to pivot a predetermined angle about the pin before a flange on the relief structure contacts the side of the stub arm. Preferably, the angle of handle pivot is sufficient to provide a visual indication that the torque limit has been reached, and additionally pivots an amount which allows the surgeon time to let up on further application of torque prior to the contact between the relief structure and arm. Moreover, the pivot angle is limited by the flange and arm to prevent the handle from impacting the side of the patient's mouth.

The torque handle displaces and does not reset itself until the operator replaces it to the original position. In this regard, the ball cams out of the indent and over the end face of the stub arm to temporarily lodge on an angled side surface. The side surface is preferably angled so as to cause the ball to tend to roll or slide in a direction across the surface away from the original handle position. Thus, when the relief structure contacts the side of the stub arm, the handle is biased in an offset position. A slight return force on the handle is all that is necessary to move the ball off the angled side surface and reset the torque wrench.

Advantageously, when the torque arm "breaks out" of the indent, the ball rolls out of the indent decreasing frictional resistance for a smooth operational feel. Additionally, the rolling contact between the ball and arm surfaces reduces wear, extending the accurate operational life of the wrench.

Additionally, when the torque handle "breaks out" of the cam, a distinctive audible click is heard. This is another indication to the surgeon that the pre-set torque has been reached in addition to the large off-set angle the handle makes with the arm.

The set screw, spring, plunger and ball form an adjustable torque mechanism by increasing the spring force on the plunger. Various settings of the torque "break out" calibration may be obtained with the assistance of commercially available torque measuring devices.

BRIEF DESCRIPTION OF THE DRAWINGS

FIG. 7 is a cross-sectional view of the cam member taken along line 7—7 of FIG. 6.

DESCRIPTION OF THE PREFERRED EMBODIMENTS

Figure 1:
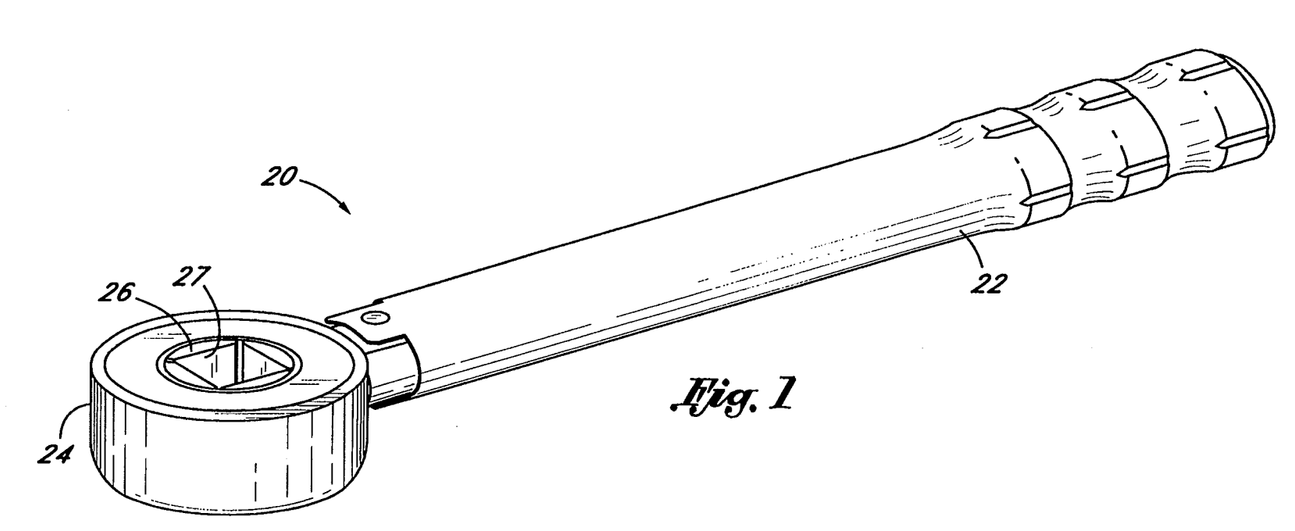
FIG. 1 is an top perspective view of the torque wrench of the present invention.

Referring to FIG. 1, an improved torque wrench 20 generally comprises a handle 22 pivotably connected at one end to a head 24 containing a tool driver 26. An interior tool-contacting surface 27 of the tool driver 26 typically has a square configuration for receiving a square male portion of a tool. Alternatively, the driver tool-contacting surface 27 may be replaced with a box wrench or other torque-applying configuration.

Figure 2:
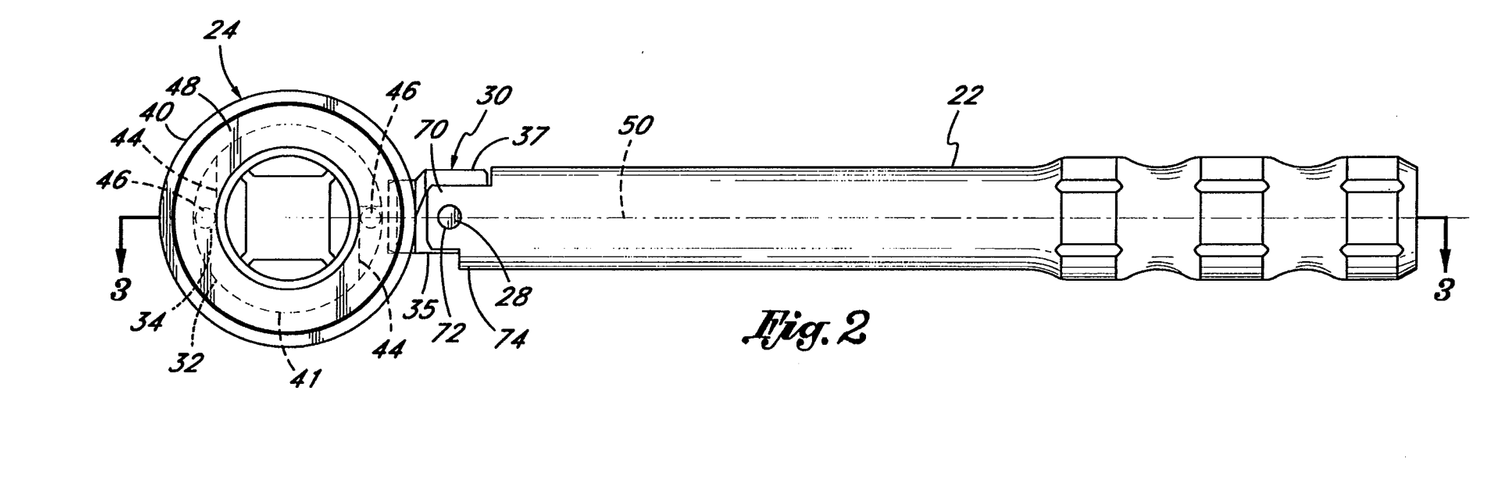
FIG. 2 is a top plan view of the torque wrench of FIG. 1.

With reference to FIG. 2, the handle 22 pivots about a pin axis formed by a pin 28 which extends through a cam member or stub arm 30 rigidly attached to the head 24. In operation, the torque wrench 20 is designed so that the handle 22 acts as a lever to turn a tool or tighten a nut (not shown) centered underneath the head 24 until a certain reaction torque is reached and the handle pivots a short arc about the pin 28 signalling the operator that the torque limit has been reached.

Figure 3:
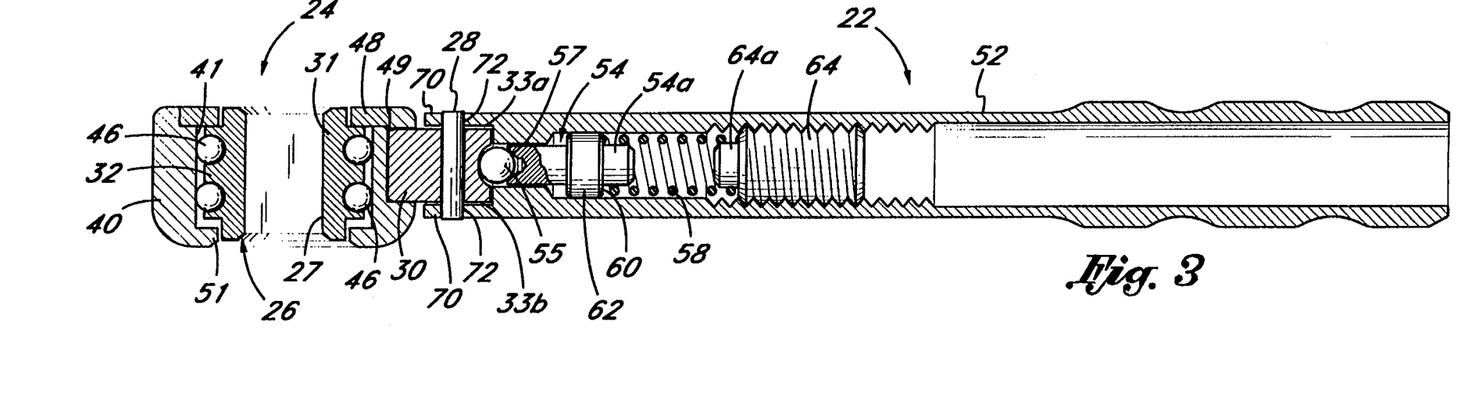
FIG. 3 is a cross-sectional view of the torque wrench taken along lines 3—3 of FIG. 2.
Figure 4:
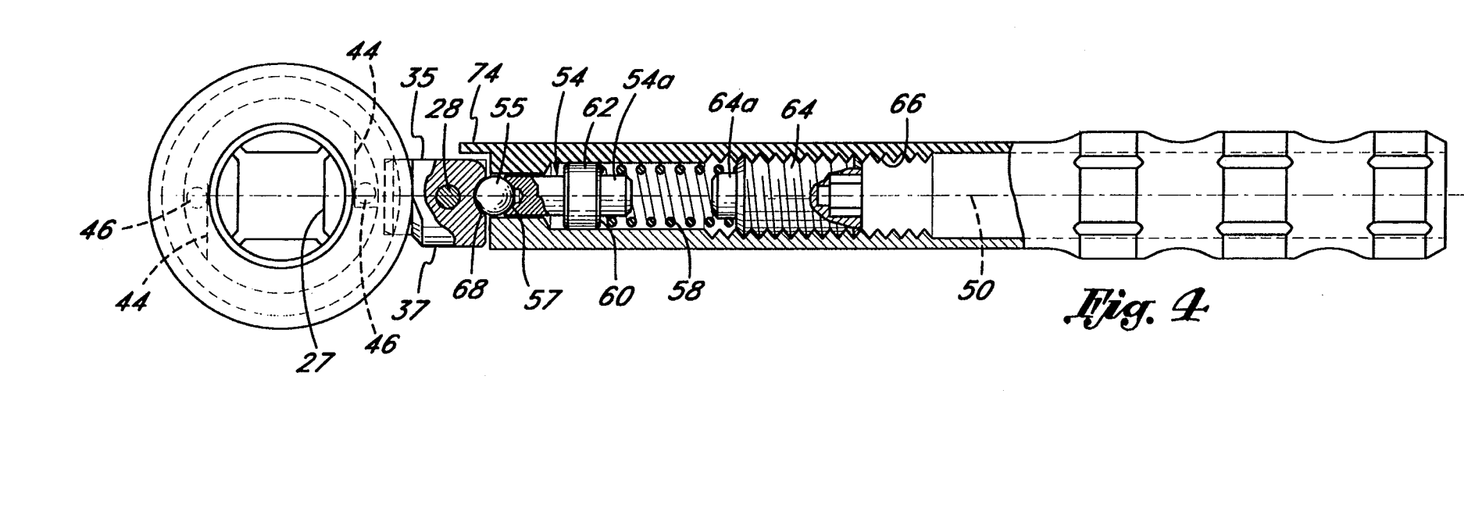
FIG. 4 is a partial cross-sectional bottom view of the torque wrench of FIG. 1 with the handle in the torque-applying position.

Now referring to FIGS. 2, 3 and 4, the head 24 generally comprises an annular outer housing 40 having an interior cylindrical wall 41 defining a cavity within which the driver 26 is free to rotate. The driver 26 includes a generally annular central portion 31 having an outer middle region 32 of larger diameter, with peripheral rounded slots 44 opened toward the cylindrical wall 41 and the inner torque-applying square surface 27. In the preferred embodiment, there are two rows of two slots 44 each, the slots in each row located diametrically opposite one another, the slots desirably at the same location in both rows. A plurality of balls 46, in this case four, are sized to slide within the slots 44. The number of balls/slots is a preferred embodiment and numerous other configurations may be employed.

The slots 44 are arranged to provide a ramp for the balls 46 such that rotation of the outer housing 40 in one direction causes the inner cylinder 41 to contact the balls and rotate them outward in the slots, compressing the balls between the cylindrical wall and the slots and providing a positive coupling between the inner driver 26 and housing.

The driving head 24, therefore, has two possible modes upon handle rotation. As can be seen in FIG. 2, a counter-clockwise movement of the torque handle 22 about the central axis of the head 24 will be free-spinning due to the balls 46 being held in the deeper portion of the slots 44, inward of the cylindrical wall 41 of the housing (shown in dashed lines). Conversely, upon clockwise rotation of the handle 22, the balls 46 rotate outward in the slots 44, thus locking the driving head 26 and housing 40 and providing a positive driving action.

The bottom of the slots 44 are cut along a line tangential to a circle about the axis of the driver 26 and extend from one side edge of the central portion 32 to a dead-end wall 34, proximate the tangent point, at which location the slots are deepest. The slots 44 have a depth at the dead-end walls 34 creating a clearance between the bottom of the slots 44 and the cylindrical wall 41 slightly greater than the diameter of the balls 46. The outer housing 40 may then rotate freely with respect to the driver 26 in the direction in which frictional contact with the cylinder 41 causes the balls 46 to move toward the dead-end walls 34. Conversely, rotation of the housing 40 in the opposite direction causes the balls 46 to migrate outward along the slots 44 to become compressed between the slots and cylindrical wall 41, thus coupling the movement of the housing to that of the driver 26.

A retainer 48 is press-fit into a circular recess 49 on the top face of the housing. The retainer 48 and an upper flange 51 of the housing 40 loosely retain the driver 26 within the cavity defined by the cylindrical wall 41.

The housing 40 receives a cylindrical projection 38 of the arm 30 in a similarly shaped recess. The arm 30 is desirably press-fit, or affixed with other well-known means, into the housing 40. An original handle axis 50, when in a torque-applying mode, is defined by the direction the arm 30 extends from the head 24.

Figures 2, 5, 6:
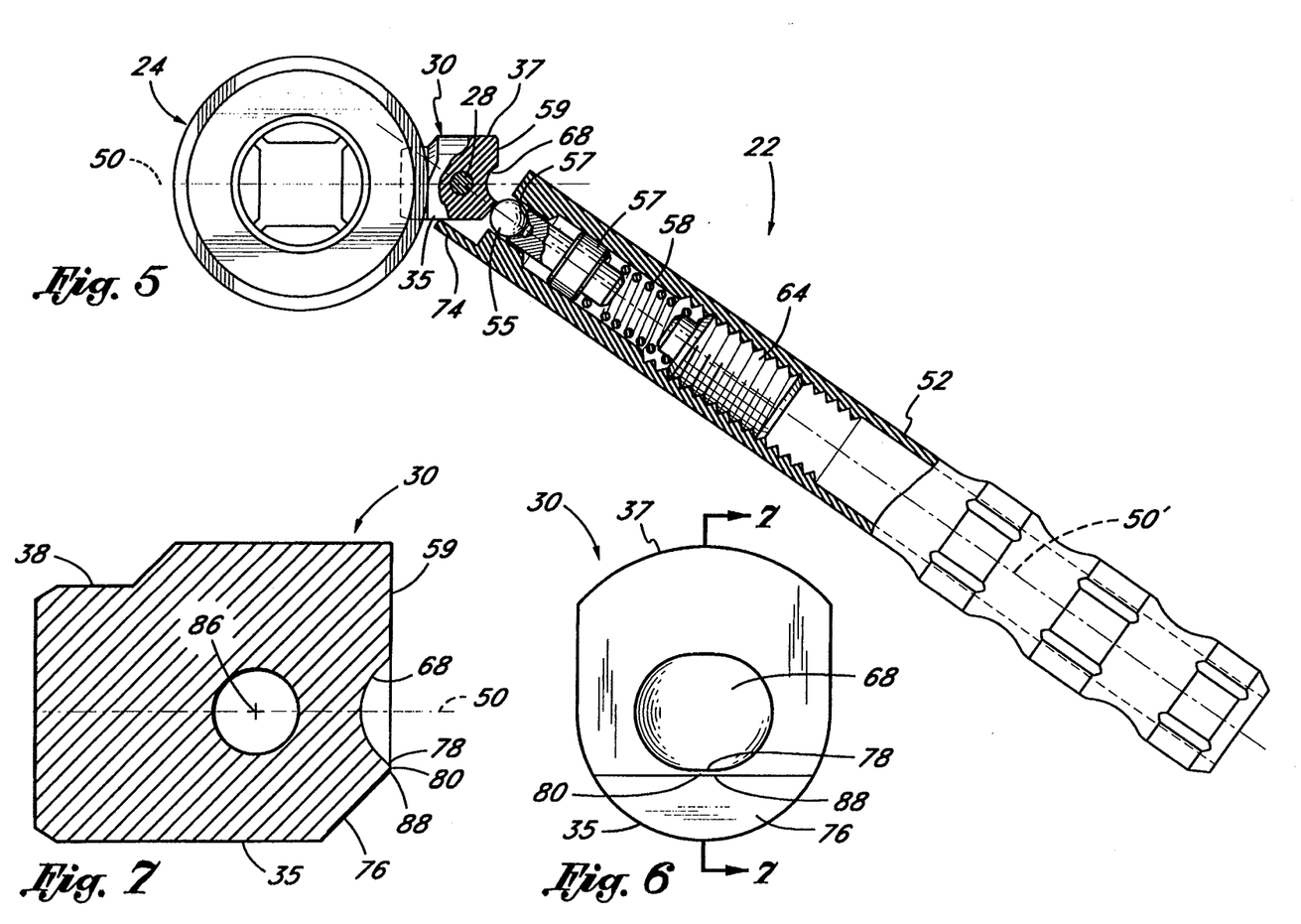
FIG. 5 is a partial cross-sectional top view of the torque wrench of FIG. 1 with the handle in an offset position indicating that a preset torque has been reached.
FIG. 6 is an elevational end view of the cam member of the torque wrench of the present invention as seen from the handle assembly.

Referring to FIGS. 3, 4 and 5, the torque handle assembly consists of a generally hollow handle body 52 having a bore 56. A plunger 54, a ball 55, a spring 58 and a set screw 64 are axially disposed within the bore 56. The plunger 54 slides longitudinally within the cylindrical bore 56 and a cone-shaped recess 57 centers the ball 55 at the end of the plunger proximate an outer face 59 of the arm 30. The helical coil spring 58 is compressed between a shoulder 60 of an enlarged cylindrical flange 62 of the plunger 54 and, at the other end, against the set screw 64 sized to engage a series of female threads 66 within the bore 56 of the handle 22. The opposing ends of the spring 58 encircle centering extensions 54a, 64a on both the plunger 54 and set screw 64, respectively.

The spring 58 acts against the plunger 54 to bias the ball 55 toward a rounded indent 68 in the outer face 59 of the arm 30. A certain torque is required to "break out" the ball 55 from the indent 68 against the force of the spring 58. When the torque handle 22 is rotated in a clockwise (as seen from above in FIG. 2) direction about the head 24 during the drive mode, a pre-set calibrated reaction torque from the tool or nut being driven is reached and the ball 55 rolls or slides out of the indent 68. In this regard, the plunger 54 may have a rounded end complementary to the indent 68, thus eliminating the ball 55.

As shown in FIG. 5, the torque handle 22 displaces or "breaks out" along an offset axis 50' and does not return to a normal state aligned with the original axis 50 until the operator replaces it to the original position. When the torque handle 22 "breaks out" of the arm 30, a distinctive audible click is heard. This is an indication to the surgeon that the pre-set torque has been reached in addition to the large angle the handle 22 makes with the original handle axis 50.

The torque handle body 52 includes a relief structure on the end nearest the head 24 to allow the handle 22 to pivot a predetermined angle about the pin 28. Two diametrically opposed hinge elements 70 extend toward the head 24 from the body 52 and straddle the arm 30 to receive the pin 28 through aligned holes 72. The hinge elements 70 extend around two opposing flat sides 33a, 33b of the arm 30, as seen in FIG. 3.

As best seen in the "broken" position of FIG. 5, the handle 22 pivots to a point where a shoulder on the end of a finger or flange 74 contacts a first arcuate surface 35 of the arm 30. Desirably, the handle 22 pivots between 20° and 40° from alignment with the original axis 50 before the flange 74 contacts the arm 30, and preferably the handle pivots approximately 30° before being restricted from further pivot. The arcuate surface 35 has a radius less than that of the handle 22 and thus is recessed with respect to the handle body 52, as the axes of the arm 30 and handle are aligned, providing a relief region for movement of the shoulder flange 74. Additionally, with the handle radially aligned with the arm about the head 24, the flange 74 ends terminate at a slightly greater radial distance than the pivot axis 28, thus contributing to the relief region and maximum pivot angle. On the opposite side of the arm 30, a second arcuate surface 37 has a radius about equal to that of the handle body 52, such that its outer surface lies substantially flush with the handle body, thus preventing the handle 22 from pivoting in that direction.

Upon handle 22 rotation, the ball 55 cams up out of the indent 68 to lodge on an angled surface or chamfer 76, as best seen in FIGS. 6 and 7, and temporarily retain the handle in an off-set position. The contact between the shoulder 74 and side face of the arm 30 is designed such that the handle 22 may pivot through a relatively large angle, in the preferred embodiment 30°, to alert the user of the torque wrench that the predetermined torque has been reached. Other configurations in which the particular maximum angle, as determined by the shoulder 74 and arm 30 contact, is altered, are contemplated in the present invention. Furthermore, the present torque wrench 20 may function without a specific angle limit, the surgeon relying on his or her own reaction to the "breaking" of the handle to stop rotation.

As illustrated in FIGS. 6 and 7, the indent 68 is preferably ellipse-shaped in the outer face 59 as seen from the handle 22, with a minor axis radius equivalent to the radius of the ball 55. The minor axis of the indent 68 is aligned in the plane in which the handle 22 pivots. The ball 55 will thus be cammed out of the indent 66 over a corner 78 and past a small flat surface or land 80 to rest on the chamfer 76.

Figure 8:
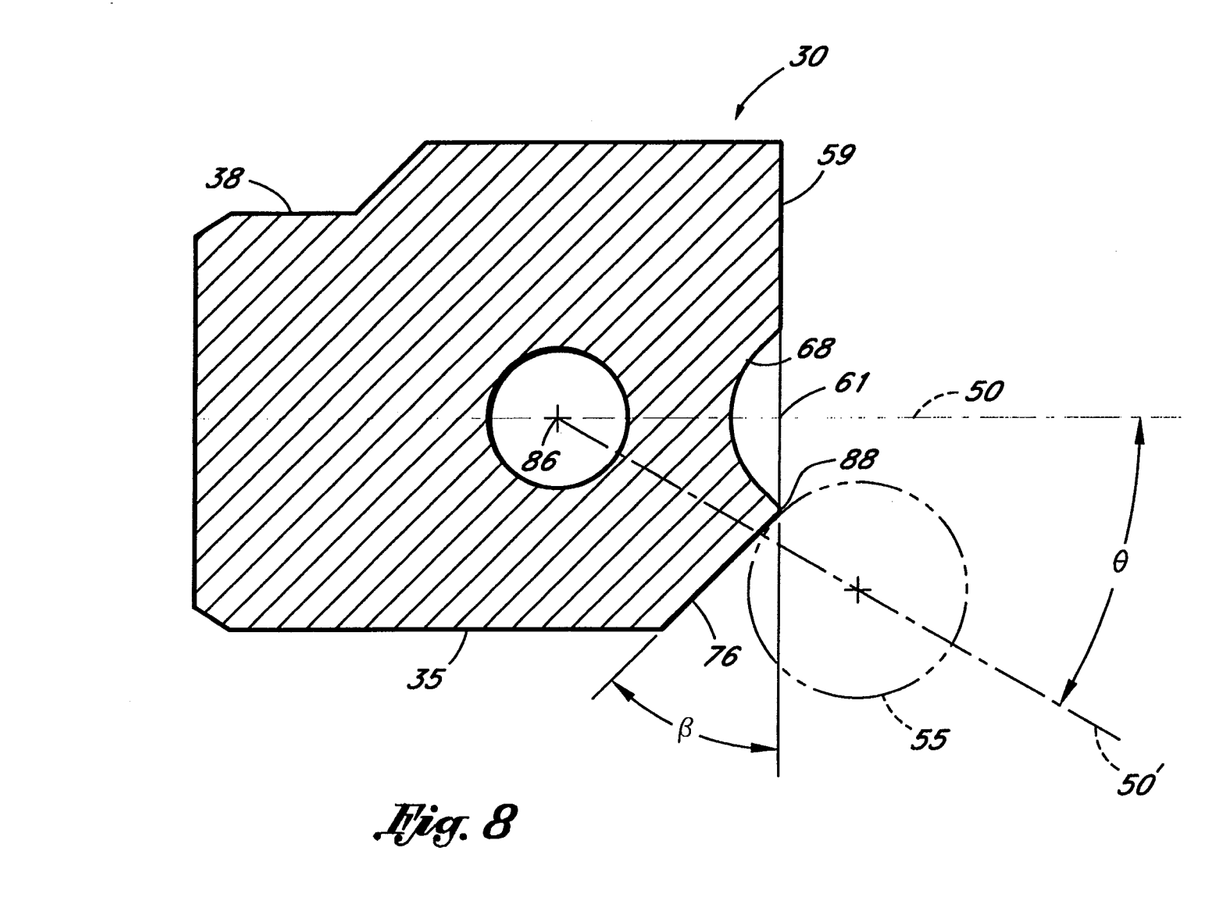
FIG. 8 is an enlarged cross-sectional view of the cam member with a ball, shown in phantom, in the position of maximum handle pivot angle.

As shown in FIGS. 7 and 8, the chamfer 76 makes a desired angle $\beta$ with the outer face 59. As can be seen in phantom in FIG. 8, the detent ball 55 rests slightly past a corner 88 between the land 80 and chamfer 76 at the maximum handle pivot, shown by the centerline 50' through the ball at an angle $\theta$ from the original handle axis 50. The angle $\beta$ of the chamfer 76 is such that the handle remains "broken" while the detent ball 55 is in contact therewith.

In the broken position of FIG. 5, the line of force from the spring 58 through the plunger 54 and ball 55 extends through the center point 86 of the pivot pin. The reaction force from the angled surface of the chamfer 76 to the ball 55 includes a component extending along the handle axis 50' and a second smaller component tangential to the arc about the pivot axis 86, creating a handle moment about the pivot axis. Thus, the chamfer 76, having a preferred angle $\beta$, retains the handle 22 in the broken position due to the slight moment created about the pivot pin 28.

The relationship between the handle pivot angle $\theta$ and the angle $\beta$ at which the chamfer 76 is machined or formed depends on a number of geometric factors and desired torque wrench characteristics. The maximum handle angle $\theta$ is generally determined first depending on the preference of the operating surgeon within certain space constraints in the patient's mouth. The size of the indent 68 and land 80 width, in combination with the linear distance from the pivot axis 86 to the outer face 59, must be chosen such that the detent ball can climb out of the indent and over the corner 88 to the chamfer 76 within the desired arc of handle pivot. It is helpful to visualize a right triangle with the hypotenuse from the pivot axis 86 to the corner 88, the run from the pivot axis to a point 61 on the original axis 50, and the rise from the point 61 along the outer face 59 to the corner 88. The angle at the pivot axis 86 between the run and the hypotenuse of this imaginary triangle must be less than the handle pivot angle $\theta$ for the detent ball 55 to reach the chamfer 76. Any number of combinations of geometries are possible to create this situation, the present embodiment being only a representative example.

The chamfer 76 must be formed at an angle $\beta$ greater than the maximum handle pivot angle $\theta$ in order to ensure the handle will not only be held in the broken position, but also biased against the physical stop between the shoulder 74 and stub arm 30. To describe the influence of the chamfered surface 76 on the handle 22, it is useful to imagine surfaces tangential to the arc about the axis 86 on which the ball 55 would rest in a static state, due to the normal force from the tangential surfaces extending directly back along the handle and against the spring 58 force line of action. Rotating a tangential surface clockwise would change the normal force on the ball 55 and cause the handle 22 to rotate clockwise.

At the corner 88, the handle axis 50' makes a predetermined angle with the original axis 50, as described above for the right triangle defined by points 61, 86 and 88. A surface tangent to the handle pivot arc makes an identical angle with the outer face 59, and the angle $\beta$ of the chamfer 76 must be greater to ensure the handle will be biased clockwise. However, as the handle 22 pivots further to the maximum angle $\theta$, a surface tangent to the handle pivot arc makes an angle with the outer face 59 which similarly increases, and the chamfered surface 76 must be oriented even further clockwise in order to maintain a clockwise bias to the handle 22. The chamfer 76 must therefore be oriented at an angle $\beta$ greater than the preferred handle pivot angle of 30°. Consequently, the angle $\beta$ is preferably between 30° and 50°, and more preferably is 45°.

A surgeon manipulating the torque wrench of the present invention will experience only a gradual change in resistance when the predetermined torque limit is reached. In this regard, as shown in the cross section of FIG. 6, the elliptical indent 68 comprises only a fraction of a circular cavity. Preferably, the radius of curvature of the line on the indent 68 in a plane through the minor axis is approximately equivalent to the radius of the detent ball 55 and the indent comprises less than a semicircle having such a radius, such that only a small portion of the detent ball extends past the outer face 59 into the indent 68. In one embodiment, the cross section through the minor axis of the indent 68 shows a portion of a circle having a 45° tangent line 90 at the intersection with the outer face 59 of the arm 30.

Furthermore, the region of the outer face 59 of the arm 30 directly adjacent to the indent 68 and in the path of the detent ball 55 comprises the flat land 80 having a width of approximately 0.005 inch. As the handle 22 pivots and the ball 55 cams out of the indent 68, the ball travels over the flat land 80 which slightly increases the compression of the spring 58 providing only a slight resistance to the travel of the ball 55. Finally, the ball 55 crosses the corner 88 between the land 80 and the chamfer 76, thereafter experiencing the small moment which retains the handle in the broken position, as described previously. The flat land 80 widens the region over which the ball 55 will repeatedly travel, thereby strengthening the area and reducing wear.

The arc of handle 22 travel, from the point at which the ball 55 rests fully within the indent 68 until the shoulder 74 contacts the side face 35 of the arm 30 at approximately 30° handle pivot, provides a transition region lengthening the time for the surgeon to react and let off on the application of pressure. The corners 78 and 88 present relatively small overall changes in angle which the ball 55 rolls over, thus reducing the stress concentrated at the corners and consequently spreading out the Hertz contact stresses applied to the ball.

For the aforementioned reasons the improved shape of the arm 30 allows the surgeon to experience a large change in handle orientation after the preset torque limit is reached and the ball 55 cams out of the indent 68 and over the flat face 80. The surgeon experiences a drop in resistance while the handle travels a noticeably large arc about the pin 28, providing sufficient time for the surgeon to let up on the torque wrench prior to the final "broken" position. The shoulder 74 contacts the side of the arm 30 to stop the travel of the ball 55 just past the point 88 between the land 80 and the chamfer 76 so that only a small reverse moment on the handle 22 is required to reset the wrench. In short, the advantageous features of the present invention provide less shock, or sudden change in feedback, to the hand of the surgeon over a larger angle resulting in a more controlled and safer operation.

In a preferred embodiment, the torque wrench handle 22 has an overall length of approximately 2.45 inches. The handle 22 may be grasped by one or more fingers and the thumb to apply the necessary torque in a controlled fashion. At the preferred maximum 30° angle off-set, the end of the handle 22 farthest from the head 24 will have moved approximately 1.22 inches laterally from the axis 50; an acceptable distance given the confines of operating in a human mouth. The torque-wrench thus is suited for dental surgery as the handle pivots a substantial arc as compared to prior devices, yet the total distance travelled is slight, due to the small size of the handle 22. It would not be apparent to adapt larger wrenches to utilize the preferred handle pivot angle of the present invention as the lateral distance the handle moves rapidly becomes awkward in larger wrenches for all but the most accessible fastening sites.

The set screw 64, spring 58, and plunger 54 form an adjustable torque mechanism for modulating the spring force on the plunger 54 which seats the ball 55 in the rounded indent 68. Various settings of the torque "break out" calibration may be obtained with the assistance of commercially available torque measuring devices. In the present invention, the preferred torque range available is from approximately 10–35 Newton-centimeters (Ncm), or 0.886–3.1 inch-pounds (inlb).

Advantageously, the elliptical indent 68 reduces the instance of sticking of the ball 55 to the indent following immersion of the wrench 20 in a sterilizing steam autoclave, which may reach temperatures of up to 275° Fahrenheit. More specifically, the ball 55 contacts the indent 68 in a line existing in a plane through the minor axis thus eliminating any surface area contact and adhering of the two members together when subsequently dried.

While the above description represents the preferred embodiment, the present invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

We claim:

1. A torque-limiting, one-way tool for installing dental implants, or the like, comprising:

a wrench head for rotating a tool, nut, screw or other element in one direction;

a stub arm rigidly attached to and extending generally radially outwardly from said head;

a tubular handle pivotally connected to said arm;

a connection on a radially outer end of said arm and a radially inner end of said handle to hold said handle generally radially aligned in driving relation with said arm, said connection being constructed to allow said handle to pivot on said arm around a pivotal axis from the radially aligned position to a pivoted position upon application of a predetermined torque on said handle in said one direction, said connection including an indent on said arm radially outer end, and a ball positioned in an end face of the radially inner end of said handle, with a spring in said handle urging said ball into engagement with said indent, said ball being adapted to move out of engagement with said indent when said handle pivots with respect to said arm;

said arm and said handle having portions that interfere to limit pivoting of said handle in said one direction after the handle has pivoted through a substantial angle sufficient to clearly tell the operator of the tool that the handle has so pivoted, and said arm and said handle having interfering portions that prevent any pivoting of the handle with respect to said arm in the opposite direction; and said arm includes a surface adjacent said indent in said one direction, said surface being oriented so that a line of force by said spring through said ball against said surface produces a moment for holding said handle in said pivoted position.

2. The tool of claim 1, wherein said surface is oriented to allow said ball to move slightly closer towards the pivotal axis of said handle, after said ball moves out of and away from said indent.

3. A torque-limiting, one-way tool for installing dental implants, or the like, comprising:

a wrench head for rotating a tool, nut, screw or other element in one direction;

a stub arm rigidly attached to and extending generally radially outwardly from said head;

a tubular handle pivotally connected to said arm;

a connection on a radially outer end of said arm and a radially inner end of said handle to hold said handle generally radially aligned in driving relation with said arm, said connection being constructed to allow said handle to pivot on said arm around a pivotal axis from the radially aligned position to a pivoted position upon application of a predetermined torque on said handle in said one direction, said connection including an indent on said arm radially outer end, and a ball positioned in an end face of the radially inner end of said handle, with a spring in said handle urging said ball into engagement with said indent, said ball being adapted to move out of engagement with said indent when said handle pivots with respect to said arm;

said arm and said handle having portions that interfere to limit pivoting of said handle in said one direction after the handle has pivoted through a substantial angle sufficient to clearly tell the operator of the tool that the handle has so pivoted, and said arm and said handle having interfering portions that prevent any pivoting of the handle with respect to said arm in the opposite direction; and said indent has a generally elliptical shape having a minor axis shorter than a major axis, said handle being mounted to pivot in a plane extending through said minor axis, the radius of curvature of said minor axis being substantially the same as the radius of said ball, the radius of curvature of said major axis being larger than the radius of said ball so that said ball has only line contact with said indent so as to facilitate smooth movement of said handle into its pivoted position.

4. A torque-limiting, one-way tool for installing dental implants, or the like, comprising:

a wrench head for rotating a tool, nut, screw or other element in one direction;

a stub arm rigidly attached to and extending generally radially outwardly from said head;

a tubular handle pivotally connected to said arm;

a connection on a radially outer end of said arm and a radially inner end of said handle to hold said handle generally radially aligned in driving relation with said arm, said connection being constructed to allow said handle to pivot on said arm around a pivotal axis from the radially aligned position to a pivoted position upon application of a predetermined torque on said handle in said one direction; and said arm and said handle having portions that interfere to limit pivoting of said handle in said one direction after the handle has pivoted through a substantial angle sufficient to clearly tell the operator of the tool that the handle has so pivoted, and said arm and said handle having interfering portions that prevent any pivoting of the handle with respect to said arm in the opposite direction; and said arm has a cross section with a pair of diametrically spaced flat sides, and said tool includes a pivot pin for said handle extending through said arm generally perpendicular to said flat sides, said arm cross section further having a pair of diametrically opposed, circularly curved sides extending between said flat sides, the radius of curvature of the curved side towards which said handle pivots being shorter than the radius of curvature of the opposite curved side.

5. A tool for installing dental implants or the like comprising:

a wrench head for rotating a tool, nut, screw or other such element in connection with installing a dental implant;

a stub arm affixed to said head and extending radially outwardly from the head;

a tubular handle having opposing hinge elements straddling said stub arm and being pivotally mounted to said stub arm on a pivot axis, said stub arm having a radially outer face with an elliptically shaped indent formed therein;

a ball positioned on a radially inner end of said handle and extending into said indent, a spring positioned within said handle biasing said ball into said indent;

said stub arm being formed to permit said handle to pivot about said pivot axis causing said ball to roll out of said indent and onto a surface of said arm adjacent the indent;

said indent elliptical shape having a minor axis lying in a plane in which said handle pivots, the curvature of said indent along said minor axis having a radius of curvature equal to the radius of said ball; and said indent elliptical shape having a major axis and a radius of curvature in the plane of said major axis greater than the radius of said ball whereby said ball has substantially only line contact with said indent when the ball is centered on said major axis, said handle being adapted to be pivoted with respect to said stub arm causing said ball to roll out of said indent onto a surface of said stub arm adjacent said indent.

6. The tool of claim 5, wherein said surface is in the form of a chamfer adapted to capture said ball in combination with the end of said handle while permitting the handle to pivot.

7. The tool of claim 6, wherein said chamfer makes an angle with said outer face of said stub arm sufficient to bias said handle in a pivoted position.

8. The tool of claim 7, wherein said chamfer makes an angle with said outer face of said stub arm greater than a maximum permissible handle pivot angle.

9. A tool for installing dental implants or the like comprising:

a wrench head for rotating a tool, nut, screw or other such element in connection with installing a dental implant;

a stub arm affixed to said head and extending radially outwardly from the head;

a tubular handle having opposing hinge elements straddling said stub arm and being pivotally connected to said arm, said arm having a radially outer face with an indent formed therein;

a ball positioned on a radially inner end of said handle and extending into said indent, a spring positioned within said handle biasing said ball into said indent;

said handle being adapted to pivot about an axis through said stub arm causing said ball to roll out of said indent and ride on a surface adjacent to said indent, said surface being oriented so that a normal force against said ball is such that said handle is biased so as to be maintained in its pivoted position with the ball out of said indent.

10. The tool of claim 9, wherein said surface is in the form of an angled surface which captures said ball in combination with the end of said handle.

11. The tool of claim 10, wherein said angled surface slopes so that said ball protrudes further from said handle as the handle moves on said surface away from said indent.

12. The tool of claim 9, wherein said radially outer face surrounding said indent is generally flat and substantially perpendicular to a centerline extending through said handle and said stub arm to the center of said head, said surface adjacent said indent including a short transition area between said indent and said angled surface.

13. The tool of claim 9, wherein said said handle includes a shoulder which limits the pivotal movement of said handle with respect to said arm in said one direction, and said handle includes a portion preventing pivotal movement of the handle with respect to said stub arm in the opposite direction.

14. A torque-limiting wrench for installing dental implants, or the like, comprising:

a wrench head for driving a tool, nut, screw or other element;

a stub arm rigidly attached to and extending generally radially outwardly from said head;

a handle pivotally connected to said arm and extending generally radially outwardly from the arm;

interengaging means on a radially outer end of said arm and a radially inner end of said handle to hold said handle generally radially aligned in driving relation with said arm enabling said arm to rotate said head upon application of torque to the arm, said interengaging means being constructed to allow said handle to pivot on said arm upon application of a predetermined torque on said handle; and said arm has a cross section with a pair of diametrically spaced flat sides, and said wrench includes a pivot pin for said handle extending through said arm generally perpendicular to said flat sides, said arm cross section further having a pair of diametrically opposed, circularly curved sides extending between said flat sides, the radius of curvature of a first curved side over which said handle pivots being shorter than the radius of curvature of a second curved side opposite said first side.

15. The tool of claim 14, wherein said arm and handle have mating surfaces on the radially outer end of said arm and the radially inner end of said handle to prevent pivoting in one direction; and wherein said handle includes a shoulder which projects radially inwardly beyond said handle interengaging means and is positioned adjacent said first curved side of said arm so that the radially inner end of said shoulder engages the first curved side of said arm to stop pivoting of said handle.

16. A torque wrench, comprising:

a handle;

a cam member pivotally connected to one end of said handle and rigidly attached to a nut driving head opposite said handle;

a spring longitudinally arranged within said handle urging a plunger toward said cam member;

a spherical surface approximately centered within said handle by said plunger and normally biased into an elliptical indent in an end of said cam member facing said handle to hold said handle radially with said head and said cam member;

a pair of hinge elements on said one end of the handle which pivot about an axis through said cam member, a first flange configured to prevent said handle from pivoting in a first direction, and a second flange which allows said handle to pivot a predetermined angle in a second direction; and a surface on a side of said cam member for receiving said spherical surface upon application of a sufficient torque on said handle to cause said handle to pivot about said axis in said second direction, said cam surface providing a reaction force on said spherical surface sufficient to hold said handle in a pivoted position.

17. The wrench of claim 16, further comprising:

a one-way ratchet driving mechanism within said head.

18. The wrench of claim 17, wherein said spherical surface is defined by a ball centered within an indent in an end of said plunger facing said cam member, said ball normally being biased into said indent and caused to slide or roll out of said indent upon application of a sufficient torque on said handle.

* * * * *